United States Patent [19]
Chiang

[11] Patent Number: 6,100,522
[45] Date of Patent: Aug. 8, 2000

[54] INTERFACE FOR LIQUID CHROMATOGRAPH AND MASS SPECTROMETER

[75] Inventor: William C. K. Chiang, Irvine, Calif.

[73] Assignee: Amway Corporation, Ada, Mich.

[21] Appl. No.: 09/097,615

[22] Filed: Jun. 15, 1998

[51] Int. Cl.[7] .................................................. G01N 30/00
[52] U.S. Cl. .......................... 250/288; 250/343; 250/281; 250/282
[58] Field of Search .................................. 250/288, 281, 250/282, 423 R, 343

[56] References Cited

U.S. PATENT DOCUMENTS

| | | |
|---|---|---|
| 3,712,111 | 1/1973 | Llewellyn ................................. 73/23.1 |
| 4,196,612 | 4/1980 | Clardy et al. . |
| 4,391,778 | 7/1983 | Andresen et al. . |
| 4,451,374 | 5/1984 | Peterson et al. . |
| 4,570,068 | 2/1986 | Sakairi et al. . |
| 4,594,159 | 6/1986 | Stalberg ............................... 210/198.2 |
| 4,594,506 | 6/1986 | Ghaderi . |
| 4,607,163 | 8/1986 | Mizuno . |
| 4,641,541 | 2/1987 | Sharp . |
| 4,863,491 | 9/1989 | Brandt et al. . |
| 4,867,947 | 9/1989 | Andresen et al. . |
| 5,281,397 | 1/1994 | Ligon et al. . |
| 5,811,059 | 9/1998 | Genovese et al. ......................... 422/89 |

*Primary Examiner*—Bruce C. Anderson
*Assistant Examiner*—Nikita Wells
*Attorney, Agent, or Firm*—Brinks Hofer Gilson & Lione; G. Peter Nichols

[57] ABSTRACT

An interface for an in-line chromatograph mass spectrometer includes a mixing tee having a first inlet, a second inlet, and an outlet with the first inlet in fluid communication with the outlet of the chromatograph; a back pressure regulator having an inlet and an outlet with the inlet in fluid communication with the outlet of the mixing tee; a coaxial splitter having an inlet, a first outlet, and a second outlet, wherein the inlet of the coaxial splitter is in fluid communication with the outlet of the pressure regulator; a mass spectrometer having an inlet in fluid communication with the first outlet of the coaxial splitter. The interface regulates the flow into the spectrometer without undesirably increasing any back pressure to the chromatograph.

13 Claims, 1 Drawing Sheet

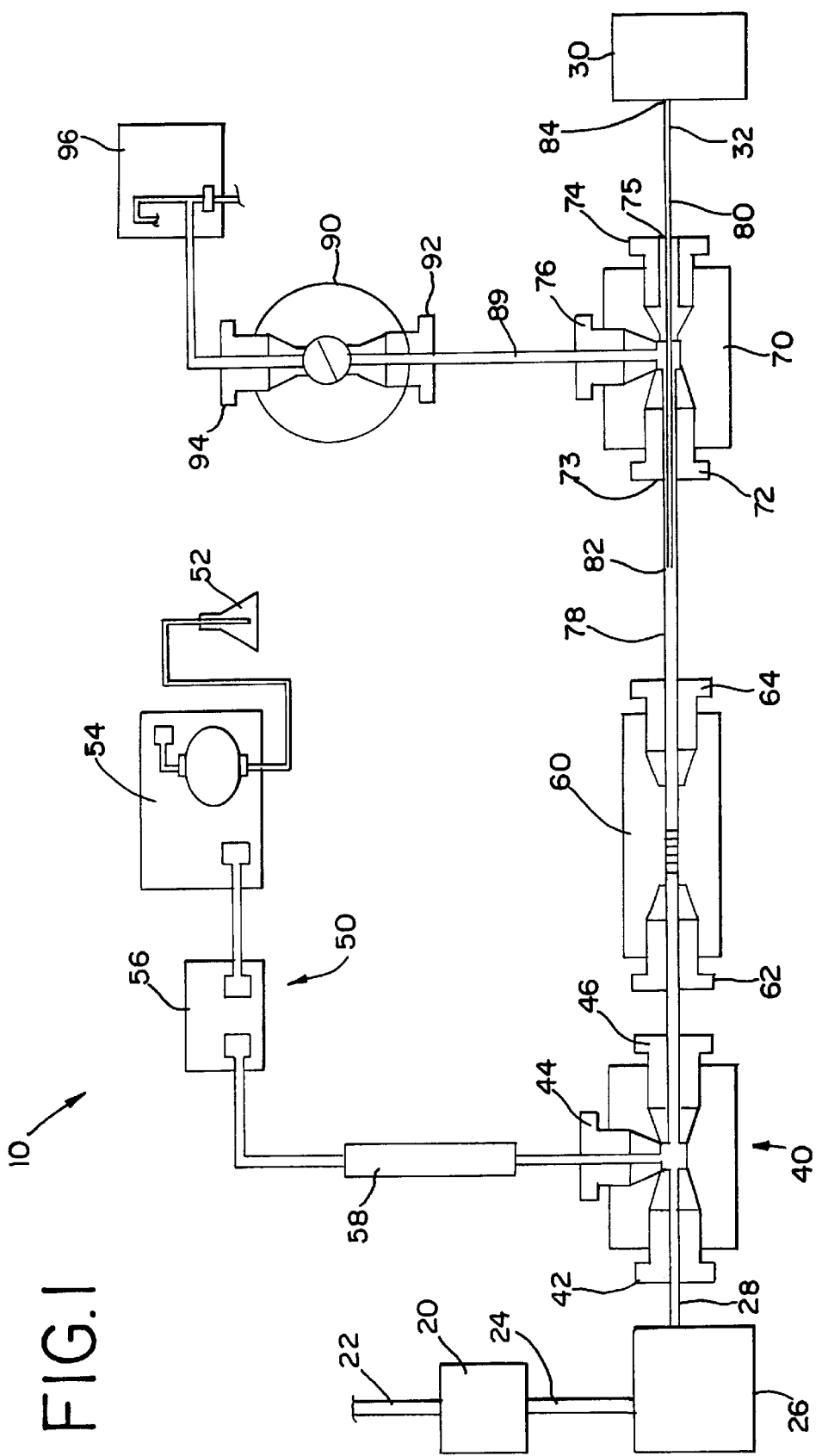

INTERFACE FOR LIQUID CHROMATOGRAPH AND MASS SPECTROMETER

BACKGROUND OF THE INVENTION

The present invention relates to an interface for an in-line liquid chromatograph and mass spectrometer.

When attempting to qualitatively and quantitatively determine the constituents of an unknown substance or substances, oftentimes, the substance is directed to a chromatograph and then either sequentially or subsequently to a mass spectrometer The chromatograph generally separates the nonvolatile components of a substance. The chromatograph, however cannot provide information such as molecular structure, mass of the sample, etc. Thus, it is generally preferred to first direct the sample to the chromatograph and then sequentially direct it to a spectrometer since a spectrometer can provide information about the mass spectra of the substance and therefore greatly facilitate the identification of the components in a substance.

One problem encountered in using such a sequential combination is that liquid chromatography columns and mass spectrometers generally have different pressure and flow requirements. For example, the high flow rates that can be encountered in a liquid chromatograph may inhibit the aerosol ionization required for the mass spectrometer. In addition, attempts to reduce the flow rate of the effluent of the chromatograph and thus, the influent of the mass spectrometer may cause a build-up of pressure greater than that which can be tolerated by the chromatograph.

One solution proposed has been to provide an interface between the chromatograph and the spectrometer. This solution, however, has not been entirely successful.

In addition, another problem exists that has not been addressed by the proposed interface. Mass spectrometers can include an atmospheric pressure chemical ionization probe or an electrospray probe. An atmospheric pressure chemical ionization probe is suitable for volatile components and stable flow is important but not critical for analysis. The electrospray probe is suitable for both volatile and non-volatile components; but stable flow is critical. Thus, it is oftentimes preferred to use both where positively charged ions may be detected in an acidic solution while negatively charged ions may be detected in a basic solution. Consequently, it is desired to modify the mass spectrometer inlet sample by mixing it with an acidic or basic solution to provide the preferred ion detection environment.

There is therefore a need for an interface for an in-line (sequential) chromatograph and mass spectrometer that regulates the inlet flow to the mass spectrometer without creating excessive back pressure and permits addition of a desired ionic solution to the sample being tested. The interface of the present invention accomplishes these desires.

SUMMARY OF THE INVENTION

The present invention relates to an in-line chromatograph mass spectrometer interface apparatus. In other words, the chromatograph is in fluid communication with the mass spectrometer such that the effluent of the chromatograph is in fluid communication with the inlet of the spectrometer. The apparatus includes a chromatograph having an inlet and an outlet; a mixing tee having a first inlet, a second inlet, and an outlet with the first inlet in fluid communication with the outlet of the chromatograph, a back pressure regulator having an inlet and an outlet with the inlet in fluid communication with the outlet of the mixing tee, a coaxial splitter having an inlet, a first outlet, and a second outlet, wherein the inlet is in fluid communication with the outlet of the pressure regulator, and a mass spectrometer having an inlet and an outlet with the inlet in fluid communication with the first outlet of the coaxial splitter.

As noted above, the present apparatus allows the chromatograph to be in fluid communication with the spectrometer; yet, allows the addition of ionic solutions to the sample being analyzed.

Desirably, the apparatus of the present invention also includes a means for effectively reducing the volume of the influent sample to the spectrometer without causing an undesirable back pressure build-up at the effluent of the chromatograph. To accomplish this objective, the first inlet of the coaxial splitter has a first inner diameter and the first outlet of the coaxial splitter has a second inner diameter smaller than the first inner diameter. Preferably, a hollow tube is disposed within the inner diameter of the coaxial splitter so that a portion of the fluid sample flows into and through the hollow tube, while another portion flows around the tube. In particular, the tube has a first end disposed adjacent the first inlet of the coaxial splitter and a second end extending through the outlet of the coaxial splitter and in fluid communication with the inlet of the spectrometer. Desirably, the outer diameter of the hollow tube is substantially the same as the second inner diameter of the coaxial splitter. As a result, the fluid not entering the inlet of the spectrometer is diverted through the outlet of the coaxial splitter without an undesirable build-up of pressure.

The present invention also contemplates a method for obtaining a mass spectrometer sample from the effluent of a chromatograph. The method includes the steps of combining a solvent with the chromatograph effluent to form a mixture and separating the mixture into a mass spectrometer sample and a waste volume. In the present method, the ratio of effluent to solvent in the mixture is from about 1:20 to about 20:1. The mass spectrometer sample has a volume from about 1% to about 90% by volume of the mixture.

The method can further include the steps of combining the solvent with the chromatograph effluent in a mixing tee wherein the effluent enters the mixing tee in a first inlet and the solvent enters the tee in a second inlet and the mixture exits the tee through an outlet. As will become apparent from the following description, the method can further include each of the components described with respect to the apparatus. Thus, one of skill in the art will understand from the description of the apparatus that the method of obtaining a mass spectrometer sample can include each of the components.

BRIEF DESCRIPTION OF THE DRAWINGS

FIG. 1 is a schematic of one embodiment of the interface apparatus of the present invention.

DESCRIPTION OF THE PREFERRED EMBODIMENTS

Turning now to FIG. 1, a schematic of one embodiment of the interface apparatus 10 of the present invention is shown. The interface apparatus generally includes a chromatograph 20 in-line with a spectrometer 30, i.e., the outlet of the chromatograph is in fluid communication with the inlet of the spectrometer. Disposed between the effluent of the chromatograph and the inlet of the spectrometer is a back pressure regulator. Thus, the effluent, preferably a portion of the effluent, of the chromatograph enters the inlet of the spectrometer. As a result, an analysis of a fluid sample can be automatically conducted.

Preferably, the chromatograph 20 has an inlet 22 that receives a sample to be analyzed and an outlet 24 from which the sample exits the chromatograph and enters a detector 26, for example a photo diode array, from which the sample exits through outlet 28. Disposed between the outlet of the chromatograph and the inlet of the spectrometer is a back pressure regulator 60 having an inlet 62 and an outlet 64. The regulator prevents an undesirable increase in pressure at its inlet and thus prevents an undesirable increase in pressure at the outlet of the chromatograph.

Desirably, the mixing tee 40 is disposed between the outlet of the chromatograph and the inlet 62 of the back pressure regulator. The mixing tee 40 has a first inlet 42, a second inlet 44 and an outlet 46. The first inlet 42 is in fluid communication with the effluent of the chromatograph.

The second inlet 44 is in fluid communication with a fluid or mixing solvent source 50. The mixing solvent is a fluid that can be added to the effluent of the chromatograph to increase the detection sensitivity of the spectrometer. The fluids that can be used are well known by those of skill in the art. For example, without being limited, the fluid may be formic acid in methanol.

The mixing solvent source includes a reservoir 52 for storing, and optionally mixing, the fluid and a pump 54 to deliver the fluid from the reservoir to the second inlet 44 of the mixing tee. The pump can be any pump suitable for delivering fluid in relatively small amounts at a substantially constant rate. For example, a pulse or isocratic pump may be suitable. Such pumps can deliver fluid at a rate from about 0.01 ml/min to about 10 ml/min.

To provide a more stable flow of fluid, a pulse damper 56 and/or a column 58, such as a chromatograph column, may be placed between the effluent of the pump and the inlet of the mixing tee. The selection and design of the pulse damper and column are well known to those of skill in the art.

The mixing solvent fluid is therefore delivered to the second inlet of the mixing tee and intimately mixed with the effluent of the chromatograph. It will be appreciated that the ratio of mixing solvent fluid to chromatograph effluent exiting the mixing tee depends on the flow rates of each. Desirably, the ratio of mixing solvent fluid to chromatograph fluid exiting the mixing tee is from about 20:1 to about 1:20, preferably from about 10:1 to about 1:10, more preferably from about 5:1 to about 1:5, most preferably from about 2:1 to about 1:2.

As noted above, fluid exits the mixing tee through the outlet 46, which is in fluid communication with the inlet 62 of the back pressure regulator. The back pressure regulator has an inlet 62 and an outlet 64, with the outlet in fluid communication with the inlet 32 of the spectrometer.

The back pressure regulator that can be used in the present invention is a variable back pressure regulator that is commonly available. The regulator is selected so that it maintains the pressure at the inlet of the regulator to less than about 1,000 psi, preferably less than about 500 psi, and more preferably less than about 100 psi. As a result, adequate mixing of the solvent and the chromatograph effluent is achieved and at the same time the turbulence caused by the combination of the effluent and solvent is reduced.

The outlet 64 of the back pressure regulator is in fluid communication with the inlet 72 of the coaxial splitter 70 through piping 78. The coaxial splitter 70 includes an inlet 72, a first outlet 74 and a second outlet 76. The inlet and first outlet are aligned in the same plane. The inlet 72 and the first outlet 74 have an inner diameter 73, 75, respectively. The piping 78 has an outer diameter 77 substantially the same as the inner diameter of the inlet 72.

Disposed within the piping and extending through the coaxial splitter is a small diameter tubing 80. The tubing 80 has an inlet 82 that may extend beyond the inlet of the coaxial splitter and an outlet 84 that is in fluid communication with the inlet 32 of the spectrometer. The tubing has an outer diameter 81, and thus an inner diameter 83 smaller than the inner diameter 79 of the piping. As a result, a portion of the fluid flowing from the effluent of the back pressure regulator through the piping enters the tubing while the other portion flows around the outer diameter of the tubing and exits the second outlet 76 of the coaxial splitter.

In addition, the inner diameter 75 of the first outlet 74 of the coaxial splitter is substantially the same as the outer diameter 81 of the tubing so that no fluid exits the second outlet 74 except through the tubing. Thus, as noted above, the portion of fluid not entering the tubing must exit the coaxial splitter through the second outlet.

It will be appreciated by one of skill in the art that by varying the diameters of the tubing in relation to the inner diameter of the piping the amount of fluid entering the spectrometer can be varied. As a result, the appropriate volume of fluid can be provided to the spectrometer.

In a preferred embodiment, the piping 78 has an inner diameter from about 0.005 to about 0.1, preferably from about 0.01 to about 0.05, more preferably from about 0.01 to about 0.03, most preferably about 0.02 inches. In this preferred embodiment, the tubing has an inner diameter from about 0.001 to about 0.05, preferably from about 0.003 to about 0.01, more preferably from about 0.004 to about 0.008, most preferably about 0.006 inches.

As a result, the amount of fluid exiting the first outlet of the coaxial splitter is from about 1% to about 90%, preferably from about 1% to about 50%, more preferably from about 1% to about 20% of the fluid entering the coaxial splitter.

In one embodiment, a second piping 89 is provided in the second outlet of the coaxial splitter. The second piping preferably has an inner diameter smaller than the inner diameter of the first piping to accommodate the smaller volume exiting the coaxial splitter.

To further ensure constant flow and fluid volume is provided to the inlet of the spectrometer, an adjustable back pressure regulator 90 having an inlet 92 and an outlet 94 may be provided. The inlet is in fluid communication with the second outlet of the coaxial splitter, preferably by piping 89. Adjustable back pressure regulators are known and the selection of an appropriate regulator is well within the knowledge of one of ordinary skill in the art. Desirably, the regulator can be adjusted from about 0 to about 500 psi, preferably from about 0 to about 300 psi and more preferably from about 0 to about 200 psi.

To better control the flow to the spectrometer, a flow meter 96 may be provided in fluid communication with the outlet of the adjustable back pressure regulator 90.

The apparatus of the present invention therefore provides a method for obtaining or providing a sample for a mass spectrometer from the effluent of a chromatograph. The method includes the steps of passing the effluent of the chromatograph into a mixing tee; combining a solvent with the effluent to form a mixture; separating the mixture into a mass spectrometer sample and waste. In this method the ratio of effluent to solvent fluid in the mixture is from about 20:1 to about 1:20, preferably from about 10:1 to about 1:10, more preferably from about 5:1 to about 1:5 and most preferably from about 2:1 to about 1:2. The mass spectrometer sample volume is from about 1% to about 90% of the mixture, preferably from about 1% to about 50%, more preferably from about 1% to about 20%.

Of course, one of skill in the art will understand that the method can include additional steps that incorporate one or more components of the above-described apparatus. For example, the effluent may enter the first inlet of the mixing tee and the solvent may be delivered to the second inlet of the mixing tee by a fluid source. The mixture may be delivered to the inlet of a back pressure regulator and then separated by a portion entering a tubing that is disposed within the piping through which the mixture flows. The tubing, as stated above, has an inner diameter smaller than the inner diameter of the piping. The tubing is in fluid communication with the inlet of the spectrometer so that the fluid entering the tubing is separated from the mixture and forms the spectrometer sample.

The method of the present invention therefore provides a simple and economical means for analyzing a sample using a spectrometer in-line with a chromatograph.

It should be understood that a wide range of changes and modifications can be made to the embodiments described above. It is therefore intended that the foregoing description illustrates rather than limits this invention and that it is the following claims, including all equivalents, which define this invention.

What is claimed:

1. An in-line chromatograph mass spectrometer interface apparatus comprising:
   a. a chromatograph having an outlet;
   b. a mixing tee having a first inlet, a second inlet, and an outlet with the first inlet in fluid communication with the outlet of the chromatograph;
   c. a back pressure regulator having an inlet and an outlet with the inlet in fluid communication with the outlet of the mixing tee;
   d. a coaxial splitter having an inlet, a first outlet, and a second outlet, wherein the inlet is in fluid communication with the outlet of the pressure regulator; and,
   e. a mass spectrometer having an inlet with the inlet in fluid communication with the first outlet of the coaxial splitter.

2. The apparatus of claim 1, wherein the second inlet of the first mixing tee is in fluid communication with a fluid source.

3. The apparatus of claim 2, further comprising a pump disposed between the fluid source and the second inlet of the mixing tee.

4. The apparatus of claim 3, wherein the pump is a pulse pump.

5. The apparatus of claim 4, further comprising a pulse dampener disposed between the pump and the second inlet of the mixing tee.

6. The apparatus of claim 5, further comprising a chromatograph column disposed between the pulse dampener and the second inlet of the mixing tee.

7. The apparatus of claim 2 wherein the back pressure regulator is a variable regulator.

8. The apparatus of claim 1, wherein the first inlet of the coaxial splitter has a first inner diameter and the first outlet of the coaxial splitter has an inner diameter smaller than the first inner diameter.

9. The apparatus of claim 8, further comprising a hollow tube having a first end and a second end, with the first end disposed adjacent the first inlet of the coaxial splitter and the second end extending through the outlet of the coaxial splitter, the tube having an outer diameter smaller than the first inner diameter, wherein a fraction of the fluid entering the first inlet passes through the outlet.

10. The apparatus of claim 1 further comprising a second pressure regulator in fluid communication with the second outlet of the coaxial splitter.

11. The apparatus of claim 9 wherein the tube has an inner diameter such that the amount of fluid exiting the first outlet of the coaxial splitter is from about 1% to about 90% of the fluid entering the coaxial splitter.

12. The apparatus of claim 11 wherein the tube has an inner diameter such that the amount of fluid exiting the first outlet of the coaxial splitter is from about 1% to about 50% of the fluid entering the coaxial splitter.

13. The apparatus of claim 11 wherein the tube has an inner diameter such that the amount of fluid exiting the first outlet of the coaxial splitter is from about 1% to about 20% of the fluid entering the coaxial splitter.

* * * * *